United States Patent [19]

Arbree et al.

[11] Patent Number: 4,468,449

[45] Date of Patent: Aug. 28, 1984

[54] PHOTOGRAPHIC PRODUCTS AND PROCESSES

[75] Inventors: Roberta R. Arbree, Nashua, N.H.; James W. Foley, Andover; Frank A. Meneghini, Arlington, both of Mass.

[73] Assignee: Polaroid Corporation, Cambridge, Mass.

[21] Appl. No.: 500,391

[22] Filed: Jun. 2, 1983

[51] Int. Cl.$^3$ .................. G03C 1/40; G03C 7/00; G03C 5/54; G03C 1/10

[52] U.S. Cl. .................. 430/222; 430/241; 430/375; 430/405; 430/446; 430/497; 430/542; 430/559; 430/564; 430/566; 430/611; 430/623; 430/955; 430/958

[58] Field of Search ............. 430/222, 223, 542, 559, 430/375, 241, 405, 445, 564, 566, 611, 623, 955, 958, 497, 446

[56] References Cited

U.S. PATENT DOCUMENTS 3,443,941  5/1969  Rogers ............................. 430/222
3,719,489  3/1973  Cieciuch et al. ................. 430/222
4,098,783  7/1978  Cieciuch et al. ................. 430/222
4,248,962  2/1981  Lau .................................. 430/559
4,358,525  11/1982 Mooberry et al. .............. 430/222

*Primary Examiner*—Richard L. Schilling
*Attorney, Agent, or Firm*—Sybil A. Campbell

[57] ABSTRACT

This invention relates to photographic processes and products for forming an image in dye from a colorless precursor of a preformed image dye which is substituted with a moiety containing a thiazolidinyl group, said thiazolidinyl group (a) being capable of undergoing cleavage imagewise in the presence of an imagewise distribution of silver ion and/or soluble silver complex and (b) possessing a substituent on the carbon atom in the 2-position that undergoes a $\beta$-elimination reaction upon said imagewise cleavage, which moiety maintains the precursor in its colorless form at least until said thiazolidinyl group undergoes said cleavage. In a further embodiment, an imagewise distribution of a photographically useful reagent, which reagent may be, for example, a photographically active reagent, is released as a carbamic acid by a $\beta$-elimination reaction following the cleavage of a thiazolidinyl group whereby said reagent is provided with a solubilizing group at least during the initial stages of processing.

25 Claims, No Drawings

PHOTOGRAPHIC PRODUCTS AND PROCESSES

BACKGROUND OF THE INVENTION

1. Field of the Invention

This invention relates to the formation of dye images from a substantially colorless precursor of a preformed image dye. In another aspect, this invention relates to photographic products and processes for providing an imagewise distribution of a reagent such as a photographically active reagent or an image dye-providing moiety and to novel compounds useful therein.

2. Description of the Prior Art

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer. Color-providing compounds useful in the above processes form the subject matter of U.S. Pat. No. 4,098,783, a continuation-in-part, of said U.S. Pat. No. 3,719,489.

Compounds disclosed in the aforementioned patents as useful in liberating a reagent in the presence of said silver ions and/or silver complex are sulfur-nitrogen compounds containing the group

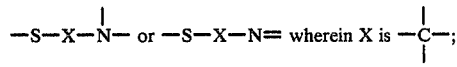

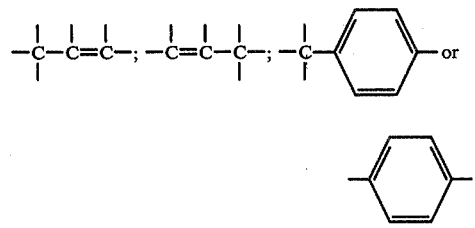

These 1,3-sulfur-nitrogen compounds may be linear or cyclic in structure, and in a particularly preferred embodiment are cyclic compounds, such as, thiazolidine compounds which comprise a colored dye radical having the chromophoric system of an azo, anthraquinone, phthalocyanine or other dye and a thiazolidin-2'-yl moiety which may be bonded directly to said dye radical or indirectly through an appropriate linking group. For example, the linking group may be —CH₂CH₂O— as in compound (33) at line 10, column 22, of said U.S. Pat. No. 3,719,489, or it may be

as in compound (34) in column 35 of said U.S. Pat. No. 4,098,783.

Copending U.S. patent application Ser. No. 500,366 of Howard G. Rogers filed concurrently herewith is concerned with the formation of a color image in a different manner using a different class of 1,3-sulfur-nitrogen compounds. Rather than relying on the differential in diffusibility between the colored parent compound and the liberated dye to form the color image, the ability of 1,3-sulfur-nitrogen compounds to undergo silver ion assisted cleavage is utilized to provide an imagewise distribution of a colored image dye from a substantially colorless precursor of a preformed image dye by employing a moiety comprising a 1,3-sulfur-nitrogen group to maintain said precursor in its substantially colorless form until said 1,3-sulfur-nitrogen group undergoes cleavage imagewise to correspond to the imagewise distribution of silver ion and/or soluble silver complex formed as a function of development of an imagewise exposed photosensitive element.

Copending U.S. patent application Ser. No. 500,415 of James W. Foley also filed concurrently herewith is concerned with yet another class of 1,3-sulfur-nitrogen compounds which may be employed to form a color image from a substantially colorless precursor of a preformed image dye. As disclosed therein, the imagewise cleavage of the 1,3-sulfur-nitrogen group is used to activate the intramolecular cleavage of an amide group for providing a corresponding imagewise distribution of a photographically useful reagent which may be colored, for example, an image dye, or colorless.

The present invention is concerned with another class of compounds which may be used in forming dye images from a substantially colorless precursor of a preformed image dye and with their use in photographic products and processes.

SUMMARY OF THE INVENTION

According to the present invention, a new class of compounds is provided wherein the imagewise cleavage of a thiazolidinyl group is used to activate a β-elimination reaction for providing a corresponding imagewise distribution of image dye from a colorless precursor of a preformed image dye. In a further embodiment, an imagewise distribution of a photographically useful reagent is released as a carbamic acid by a β-elimination reaction activated by the cleavage of a thiazolidinyl group whereby said reagent is provided with a solubilizing group at least during the initial stages of processing. The photographically useful reagent released as a carbamic acid may be colored, for example, an image dye, or colorless.

It is, therefore, one object of the present invention to provide photographic products and processes for forming a dye image from a colorless precursor of a preformed image dye which is substituted with a moiety containing a thiazolidinyl group, said thiazolidinyl group (a) being capable of undergoing cleavage imagewise in the presence of an imagewise distribution of silver ion and/or soluble silver complex and (b) possessing a substituent on the carbon atom in the 2-position that undergoes a β-elimination reaction upon said imagewise cleavage, which moiety maintains the precursor in its colorless form at least until said thiazolidinyl group undergoes said cleavage to activate said β-elimination reaction.

It is another object of the present invention to provide photographic products and processes for releasing an imagewise distribution of a photographically useful reagent as a carbamic acid.

It is still another object of the present invention to provide novel thiazolidine compounds useful in the aforesaid photographic products and processes.

Other objects of the invention will in part be obvious and will in part appear hereinafter.

The invention accordingly comprises the processes involving the several steps and the relation and order of one or more of such steps with respect to each of the others, and the product and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

In one aspect, the present invention is concerned with a photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ions and/or soluble silver complex in the partially developed and undeveloped areas of said emulsion; and forming as a function of said development a color image in dye from said colorless precursor, said colorless precursor of a preformed image dye being substituted with a moiety containing a thiazolidinyl group, said thiazolidinyl group (a) being capable of undergoing cleavage imagewise in the presence of said imagewise distribution of silver ions and/or soluble silver complex and (b) possessing a substituent on the carbon atom in the 2-position that undergoes a β-elimination reaction following by the cleavage of said thiazolidinyl group, said moiety maintaining said precursor in its colorless form at least until said thiazolidinyl group undergoes said cleavage. Preferably, the silver halide emulsion is a negative working emulsion and the color image is a positive image in dye.

The colorless image dye-providing compounds that may be employed in the above process may be represented by the formula

T—L—Y—Z (I)

wherein T is a thiazolidin-2'-yl group capable of undergoing cleavage in the presence of silver ions and/or soluble silver complex; L is a moiety capable of undergoing a β-elimination reaction following the cleavage of said thiazolidin-2'-yl group; Y is a leaving group released by said β-elimination reaction; and Z is a preformed image dye which taken with Y is a colorless precursor of said preformed image dye, said T—L— being substituted on said precursor such that the precursor is maintained in its colorless form at least until said thiazolidin-2'-yl group undergoes said cleavage.

β-elimination reactions are well known in the art and involve the breaking of bonds, for example, a C—N, C—O, C—S, C—Se, N—N, N—O or other bond to release a leaving group, which in this instance would comprise the image dye. Any moiety that undergoes β-elimination may be employed as L in formula I above, provided that the elimination rate for the moiety taken with the silver assisted cleavage rate provides the image dye at a photographically useful rate in a given photographic system. The rate constants for various leaving groups in elimination reactions of β-substituted sulphones, β-substituted phenyl ketones and β-substituted esters have been reported by Charles J. M. Stirling et al, J. Chem. Soc. (B), 1970, pages 672 and 684; Charles J. M. Stirling et al, J. Chem. Soc. Chem. Commun., page 941 (1975); and Charles J. M. Stirling, Acc. Chem. Res. 12, pages 198–203 (1979). Examples of some leaving groups from a carbon system include —SMe; —SPh; —SePh; —OPh; —OMe; —P(O)(OEt)$_2$; —NHTs; —C(Me)$_2$NO$_2$; —N(Me)Ts; —N(Me)Ac; —N(Ph)Ac; —N(Ph)Ts; —N(Ph)CO$_2$CH$_2$Ph and —N(Me)CO$_2$Ph wherein Me, Et, Ph, Ac and Ts represent methyl, ethyl, phenyl, acetyl and tosyl, respectively.

In a further embodiment of the present invention, the moiety that undergoes the β-elimination reaction comprises a carbamate group and releases an imagewise distribution of a photographically useful reagent as a carbamic acid. Compounds useful for this purpose may be represented by the formula

wherein T is a thiazolidin-2'-yl group capable of undergoing cleavage in the presence of silver ions and/or soluble silver complex; L is a moiety capable of undergoing a β-elimination reaction following said cleavage of said thiazolidin-2'-yl group to release

R is hydrogen or a monovalent hydrocarbon group, e.g., alkyl, aryl, alkaryl or aralkyl; and PHOTO is the radical of a photographically useful reagent selected from a photographically active reagent and a color-providing moiety selected from an image dye, an image dye intermediate and when taken with

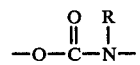

is a colorless precursor of a preformed image dye, provided that when

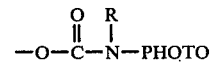

is said colorless precursor, said T—L— is substituted on said precursor such that the precursor is maintained in its colorless form at least until said thiazolidin-2'-yl group undergoes said cleavage.

Examples of photographically active reagents that may be released imagewise from the inert parent compound include a development restrainer or arrestor, a silver halide solvent, a silver halide developing agent, an antifoggant, a gelatin hardener, an emulsion stabilizer, a toning agent, an anti-bronzing agent and so forth.

The image dye released including the dyes formed from the colorless precursor compounds may comprise any of the general classes of dyes known in the art, for example, nitro, azo, xanthene and anthraquinone dyes; also leuco, indicator, temporarily "color shifted" and other dyes that take on a color change during or subsequent to processing to provide the ultimately desired color for the dye image via oxidation, changes in pH, alkaline hydrolysis of a blocking group, etc. It will be appreciated that such a color change is precluded without removal of the moiety T—L— only in those compounds where

is the colorless precursor of a preformed image dye. Where the color-providing moiety is a colored image dye as distinguished from said colorless precursor or where it is a dye intermediate, the moiety T—L— is used to provide, for example, an anchor and the dye image is formed as a result of the differential in diffusibility between the parent compound and the liberated color-providing moiety. Like the image dye released, the dye intermediate released may be any molecule as previously employed that reacts with another molecule to form a complete dye. For example, it may be a phenolic, naphtholic, methylene or other coupler and/or a molecule that reacts with a coupler, e.g., a quinonediimine or a carbonyl compound to form a complete dye.

Preferred compounds of the present invention for providing an image dye from a colorless precursor of an image dye may be represented by the formula

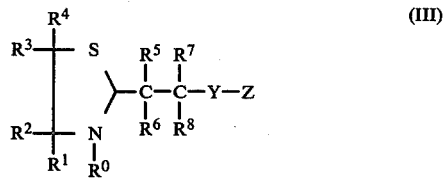

wherein $R^0$ is selected from alkyl, aryl, aralkyl and alkaryl; $R^1$ is selected from hydrogen, carboxy, N,N-dialkylcarboxamido, alkyl, aryl, aralkyl and alkaryl; $R^2$, $R^3$ and $R^4$ each are selected from hydrogen, alkyl, aryl, aralkyl and alkaryl; $R^5$ is selected from hydrogen and a group that can be removed upon cleavage of said thiazolidinyl group to leave an electron pair, e.g., a carboxy group; $R^6$, $R^7$ and $R^8$ each are selected from hydrogen, alkyl, aryl, aralkyl and alkaryl; and Y is a leaving group released by a $\beta$-elimination reaction following cleavage of said thiazolidinyl group; and Z is a preformed image dye which taken with Y is a colorless precursor of a preformed image dye.

Preferred compounds for releasing a photographically useful reagent as a carbamic acid may be represented by the formula

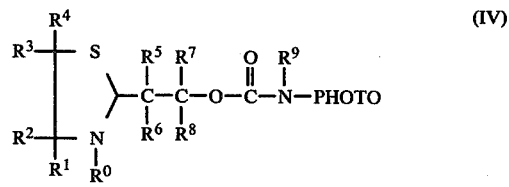

wherein $R^0$, $R^1$, $R^2$, $R^3$, $R^4$, $R^5$, $R^6$, $R^7$, $R^8$ have the same meaning given above; $R^9$ is hydrogen, alkyl, aryl, aralkyl or alkaryl; and PHOTO is the radical of a photographically useful reagent selected from a photographically active reagent and a color-providing moiety selected from an image dye, an image dye-intermediate and when taken with

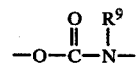

is a colorless precursor of a preformed image dye. Where

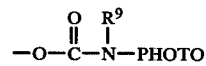

comprises the colorless precursor of a preformed image dye, it may be, for example,

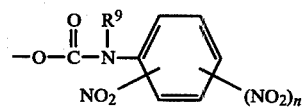

wherein $R^9$ has the same meaning given above and n is 0 or 1.

Typical aryl groups include phenyl and biphenyl and said alkyl groups comprising R, $R^0$, $R^1$, $R^2$, $R^3$, $R^4$, $R^5$, $R^6$, $R^7$, $R^8$ and $R^9$ usually contain 1 to 20 carbon atoms, such as methyl, ethyl, propyl, isopropyl, isobutyl, hexyl, dodecyl, octadecyl and eicosanyl. Said aralkyl may be, for example, phenyl-substituted alkyl wherein said alkyl usually contains 1 to 20 carbon atoms, and said alkaryl may be, for example, alkyl-substituted phenyl wherein said alkyl usually contains 1 to 20 carbon atoms. When $R^1$ is N,N-dialkylcarboxamido, each alkyl usually contains 1 to 20 carbon atoms.

It will be appreciated that the above-denoted R to $R^9$ groups may be further substituted with, for example, amino, carboxy, hydroxy, alkoxy, sulfonamido or other appropriate group.

The compounds of the present invention can be synthesized in a conventional manner, for example, by reacting a 2-substituted thiazolidine compound with another molecule comprising the selected photographic reagent to give the desired product or by reacting an aminoethanethiol with an aldehyde-substituted molecule comprising the photographic reagent to give the desired product.

The following examples are given to further illustrate the present invention and are not intended to limit the scope thereof.

EXAMPLE 1

Preparation of the compound having the formula

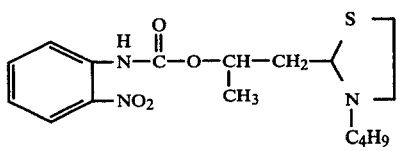

One gram of the following carbamoyl chloride-isocyanate mixture

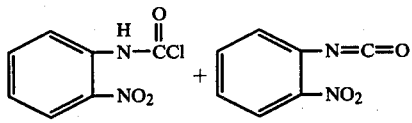

was added to approximately 20 ml of dry chloroform. To this mixture was added one gram of the thiazolidine alcohol of the formula

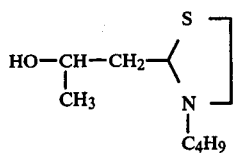

This reaction mixture was stirred at room temperature for two hours. Additional chloroform solvent was added so that any starting material present as the HCl salt would be soluble. TLC in ether was recorded. The reaction mixture was evaporated and triturated with ether. The insoluble solid was presumed to be the HCl salt of the title compound. TLC had shown a considerable amount of dark material which remained at the origin, so the solid was chromatographed on silica with chloroform as eluent. The amine and the title compound came off with the front as a mixture. TLC showed a minor amount of amine plus another colored impurity. NMR showed mostly title compound that came off as free base. The free base was soluble in ether and positions in NMR compared with those of the starting alcohol (free base).

The thiazolidine alcohol having the formula set out below was prepared as follows:

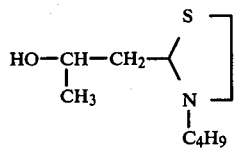

A mixture of 2-n-butylaminoethanethiol (4.5 g; 0.034 mole) and the dimer of β-hydroxy-n-butyraldehyde (3.0 g; 0.017 mole) in approximately 100 ml of benzene were refluxed under nitrogen using a Dean-Stark trap to remove water. (Water began to come over immediately and stopped after about 20 minutes.) Refluxing of the mixture was continued for one hour and then the benzene was removed by evaporation. The residue was distilled (boiling point 100° C. at 0.125 mm) to give the title compound as a colorless oil. These thiazolidine intermediates form the subject matter of copending U.S. patent application Ser. No. 474,144 of Robert R. Arbree, William J. Cumming and Frank A. Meneghini filed Mar. 9, 1983.

EXAMPLE 2

Preparation of the compound having the formula

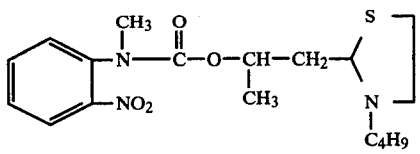

The compound of Example 1 (200 mg; 0.54 mmole) in 0.5 ml of anhydrous N,N-dimethylformamide (over 4A sieves) was added to sodium hydride (13 mg; 0.54 mmole) in N,N-dimethylformamide under nitrogen. After stirring at room temperature for 1½ hours, evolution of hydrogen had ceased. Methyl iodide (77 mg; 0.54 mmole) dissolved in N,N-dimethylformamide was added dropwise. Heat evolved. Stirring of the reaction mixture was continued at room temperature. Sodium iodide precipitated. The solution of the carbamate anion was red. As the reaction with methyliodide proceeded, the color changed to orange. The time for complete color change was about 1½ hours. Thereafter, the mixture was poured into water, extracted with ether, the ether extract washed several times with water, dried and evaporated. The yield of title compound was nearly quantitative.

EXAMPLE 3

Preparation of the compound having the formula

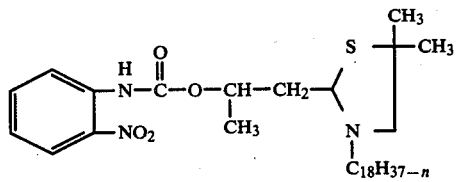

The thiazolidine alcohol of the formula,

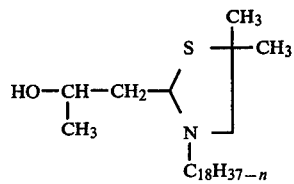

(1.85 g) was dissolved in about 25 ml dry chloroform. Solid o-nitrophenyl isocyanate was added, and the reaction mixture was stirred over the weekend. It was then evaporated, and the oil residue was dissolved in petroleum ether and extracted about five times with water. The petroleum ether layer was dried and evaporated. (NMR showed the desired product.) Some solid formed in the oil. It was insoluble in petroleum ether and was removed by dissolving the product in petroleum ether and filtering. Evaporation of the petroleum ether gave an orange oil which crystallized on standing. The crystals were slightly soluble in isopropanol. The partially crystalline oil was triturated with isopropanol, filtered and the crystals washed with isopropanol and dried to give approximately 400 mgs of the title compound as pale yellow crystals (melting range 53°-55° C.

EXAMPLE 4

Preparation of the compound having the formula

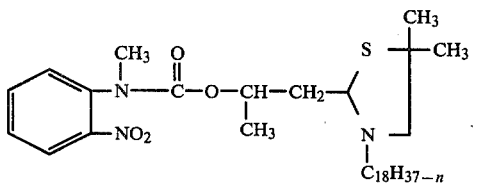

The compound of Example 4 was prepared from the compound of Example 3 (1.1 g; 1.86 mmole) according to the procedure given in Example 2 using equimolar amounts, i.e., 1.86 mmole of both sodium hydride and methyl iodide in N,N-dimethylformamide. Evaporation of the ether extract of the reaction mixture gave an orange oil. TLC showed the title compound as the major product (which changed to orange in several hours) plus a very minor amount of two yellow impurities.

As noted previously, in one embodiment the present invention is concerned with the formation of a color image from certain colorless image dye-providing compounds comprising a colorless precursor of a preformed image dye. In this embodiment, the colorless compound may be present initially in the photosensitive element in a layer or layers other than the layer containing the light-sensitive silver halide emulsion, or it may be in the light-sensitive layer itself. For example, it may be in a layer on one side of the emulsion or in two layers, one on either side of the emulsion. If desired, it may be separated from the emulsion layer by one or more spacer layers. Where the colorless compound is present in the light-sensitive layer, the compound should be inert, that is photographically innocuous in that it does not adversely affect or impair image formation. If not photographically innocuous, the compound may be modified in a manner which does not interfere with the development process in any way, but which deactivates the compound so that it does not affect adversely the light-sensitive emulsion. Rather than being disposed in the photosensitive element, the colorless compound may be initially contained in a layer associated with an image-receiving layer in processes such as diffusion transfer processes where image-receiving elements are employed.

The formation of color images according to the subject invention is applicable to the preparation of both monochromatic and multicolor images. For example, the colorless image dye-providing compounds of this invention may be employed in photographic systems utilizing multilayer photosensitive elements comprising at least two selectively sensitive silver halide emulsion strata having said colorless image dye-providing compounds associated therewith which are processed simultaneously and without separation to provide a multicolor image. In such a structure, a barrier interlayer of silver complex scavenger, e.g., silver precipitant may be used, to confine diffusion of soluble silver complex to the appropriate stratum. Also, filter layers containing, e.g., bleachable filter dyes of the type described in U.S. Pat. Nos. 4,304,833, 4,358,118 and 4,304,834 may be used to control the spectral composition of light falling on the underlying light-sensitive layer. Another useful structure for obtaining multicolor images is the screen type negative described in U.S. Pat. No. 2,968,554 or that described in U.S. Pat. No. 3,019,124.

According to one method of forming color images, both the image dyes and their colorless parent compounds comprising the colorless precursor of a preformed image dye are substantially non-diffusible from their initial position in association with the photosensitive strata. To achieve the requisite non-diffusibility, the colorless parent compound may be appropriately substituted with an immobilizing group, e.g., a long chain alkyl group and the image dye released may be a dye that is substantially non-diffusible by nature or it may be rendered non-diffusible by appropriate substitution with an immobilizing group, by including a mordant in the same layer with said image dye or by other means that would prevent the dye from diffusing from the photosensitive element.

Though the developed silver present in the photosensitive element after image formation and any remaining silver halide may be removed in a conventional manner, for example, by a bleach-fix bath, it is preferred to bleach the developed silver and to complex residual silver halide in situ. In a particularly preferred embodiment, the silver halide emulsion employed is one which upon development contains low covering power silver in the developed areas whereby the need for bleaching is obviated. In these embodiments, it will be appreciated that the silver halide developing agents, the silver halide solvents and other reagents employed should be substantially non-staining.

Rather than forming monochromatic and multicolor images non-diffusible from the photosensitive element, it will be appreciated that the image dyes provided by the colorless parent compounds may be diffusible to form the color image on a single common image-receiving layer. In this embodiment, the subsequent formation of a color transfer image preferably employs a differential in diffusibility between the colorless parent compound and the liberated dye. This differential in diffusibility may be achieved in a known manner by the appropriate selection of an immobilizing group(s), such as a long chain alkyl or alkoxy group and/or solubilizing group(s), such as, hydroxy, carboxy or sulfo groups.

In the latter embodiments, where the image dyes released are diffusible, the photosensitive layer and the image-receiving layer may be in separate elements which are brought together during processing and thereafter retained together as the final print or separated following image formation, or the photosensitive and image-receiving layers may be in the same element. For example, the image-receiving layer may be coated on a support and the photosensitive layer coated on the surface of the image-receiving layer. The processing composition may be applied to the combined negative-positive element using a spreader sheet to facilitate spreading the liquid composition in a uniform layer adjacent the surface of the photosensitive layer. The image-receiving layer carrying the color image may be separated from the overlying photosensitive layer(s), e.g., with the aid of a stripping layer, or the color image may be viewed as a reflection print by employing a light-reflecting layer between the photosensitive and image-receiving layers.

Illustrative of still other film units are those where the negative and positive components together comprise a unitary structure and are laminated and/or otherwise physically retained together at least prior to image formation. Generally, such film units comprise a plurality of layers including a negative component comprising at least one light-sensitive layer, e.g., a silver halide layer and a positive component comprising an image-receiving layer which components are laminated together or otherwise secured together in physical juxtaposition as a single structure.

Included among such structures are those adapted for forming a transfer image viewable without separation, i.e., wherein the positive component containing the transfer image need not be separated from the negative component for viewing purposes. In addition to the aforementioned layers, such film units include means for providing a reflecting layer between the image-receiving and negative components in order to mask effectively the silver image or images formed as a function of development of the silver halide layer or layers and also to provide a background for viewing the transfer image in the receiving component, without separation, by reflected light. This reflecting layer may comprise a preformed layer of a reflecting agent included in the film unit or the reflecting agent may be provided subsequent to photoexposure, e.g., by including the reflecting agent in the processing composition.

The aforementioned layers are preferably carried on a support and preferably are employed with another support positioned on the opposed surface of the layers carried by the first support so that the layers are sandwiched or confined between the support members, at least one of which is transparent to permit viewing of the final image. Such film units usually are employed in conjunction with means, such as, a rupturable container containing the requisite processing composition and adapted upon application of pressure of applying its contents to develop the exposed film unit. Film units of this type are now well known and are described, for example, in U.S. Pat. Nos. 3,415,644, 3,415,645, 3,415,646, 3,594,164 and 3,594,165.

The processing composition employed comprises an aqueous solution and usually, an aqueous alkaline solution of a silver halide developing agent and a silver halide solvent. The named ingredients may be present initially in the aqueous medium or may be present initially in the photographic film unit, for example, in the emulsion and/or image-receiving and/or spacer layers as heretofore suggested in the art. When such ingredients are present initially in the film unit, the processing composition is formed by contacting the product with a suitable aqueous medium to form a solution of these ingredients.

The alkali employed may be any of the alkaline materials heretofore employed, such as sodium or potassium hydroxide and like the developing agent and the solvent may be initially in a layer or layers of the film unit.

The silver halide solvent also may be any of the heretofore known materials, such as sodium or potassium thiosulfate, sodium thiocyanate or uracil; also the thioether-substituted uracils, pseudo-uracils and other compounds disclosed and claimed in U.S. Pat. No. 4,126,459; the 1,3-disulfonylalkanes and cycloalkanes of U.S. Pat. Nos. 3,769,014 and 3,958,992, respectively; or the alkanes containing an intralinear sulfonyl group and, e.g., an intralinear N-tosylsulfimido or N-tosylsulfoximido group as disclosed and claimed in U.S. Pat. No. 4,107,176. Also, a silver halide solvent precursor may be used such as those disclosed in U.S. Pat. No. 3,698,898 and as disclosed and claimed in copending U.S. patent application Ser. No. 382,479 filed May 27, 1982.

Examples of silver halide developing agents that may be employed are hydroquinone and substituted hydroquinones, such as tertiary butyl hydroquinone, 2,5-dimethyl hydroquinone, methoxyhydroquinone, ethoxyhydroquinone, 4'-methylphenylhydroquinone; pyrogallol and catechols, such as catechol, 4-phenyl catechol and tertiary butyl catechol; aminophenols, such as 2,4,6-diamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid and other enediols, such as, tetramethyl reductic acid; hydroxylamines, such as N,N-di-(2-ethoxyethyl)hydroxylamine, N,N-di-(2-methoxyethyl)hydroxylamine and N,N-di-(2-methoxyethoxyethyl)hydroxylamine; and heterocyclic compounds, such as, 1-phenyl-3-pyrazolidone and 4-methyl-4-hydroxymethyl-1-phenyl-3-pyrazolidone.

Usually, though not necessarily, the processing composition includes a viscosity-increasing reagent such as a cellulosic polymer, e.g., sodium carboxymethyl cellulose, hydroxyethyl cellulose, carboxymethyl hydroxyethyl cellulose, etc; an oxime polymer, e.g., polydiacetone acrylamide oxime; or other high molecular weight polymers.

In addition to the aforementioned ingredients, the processing composition also may contain antifoggants, preservatives and other materials as conventionally used in the art.

The processing composition may be applied to the photosensitive element, for example, by coating, dipping, spraying or by the use of a rupturable container or pod such as disclosed in U.S. Pat. No. 2,543,181, the container being positioned in the film unit so as to be capable upon rupturing of spreading its contents in a substantially uniform layer.

The photosensitive element may be any of those conventionally employed and generally comprises a silver halide emulsion carried on a base, for example, glass, paper or plastic film, such as cellulose triacetate film, polyethylene terephthalate film, polystyrene film and polyolefin films, e.g., polyethylene and polypropylene films. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Depending upon the particular photographic system, a mordant for the dye image may be used in association with the photosensitive layers as discussed above, or a separate image-receiving element may be employed. The image-receiving layer, i.e., dyeable stratum may comprise any of the materials known in the art, such as polyvinyl alcohol, gelatin, etc., preferably containing a mordant for the transferred image dye(s). The dyeable stratum can be in the same element as the photosensitive layer or it may be in a separate element as appropriate for a given photographic process.

In diffusion transfer processes employing an aqueous alkaline processing composition, it is well known to employ an acid-reacting reagent in a layer of the film unit to lower the environmental pH following substantial dye transfer in order to increase the image stability. For example, the previously mentioned U.S. Pat. No. 3,415,644 discloses systems wherein the desired pH reduction may be effected by providing an acid-reacting layer adjacent the dyeable stratum. These layers may comprise polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent to the silver halide most distant from the image-receiving layer. Another system for providing an acid-reacting reagent is disclosed in U.S. Pat. No. 3,576,625.

An inert interlayer or spacer layer may be disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

The acid-reacting layer and associated spacer layer are usually contained in the image-receiving element in systems wherein the dyeable stratum and photosensitive strata are contained on separate supports, e.g., between the support for the receiving element and the dyeable stratum. In integral film units, these layers may be associated with the dyeable stratum, e.g., on the side of the dyeable stratum opposed from the photosensitive element or, if desired, they may be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing composition.

In addition to the aforementioned layers, the film units may contain additional layers as commonly used in the art, such as a layer of antihalation dye, and/or a layer of filter dye arranged between differentially color-sensitive emulsion layers. Depending upon the particular photographic system, it may be desirable to use antihalation and filter dyes which become decolorized during photographic processing.

It will be understood that in the other embodiments of the present invention where the parent compound releases, for example, a photographically active reagent, the parent compound may be disposed either in the photosensitive element or in a second element depending upon the particular photographic system and the photographic reagent to be released. The parent compound and the reagent released can have the same or different mobility characteristics as may be required for a given process. As discussed above, the respective mobilizing characteristics can be adjusted in a known manner by appropriate substitution with immobilizing and/or solubilizing groups. Depending upon the particular parent compound, it may be advantageous to employ a combination of immobilizing and solubilizing groups to render the compound non-diffusible yet more wettable in the processing composition. Where it is desired to release, for example, a diffusible dye from a colored substantially non-diffusible parent compound anchored with a single immobilizing group, the anchor should be positioned on the parent compound such that upon cleavage, it will be on a fragment different from the fragment released as the diffusible color-providing moiety. Also, it may be preferable to position the immobilizing group on that portion of the parent compound that ultimately forms a complex with the silver ion upon cleavage.

The following examples show by way of illustration, and not by way of limitation, the utility of the subject compounds.

EXAMPLE I

Two photosensitive elements were prepared by coating a gelatin subcoated polyethylene terephthalate film base with a gelatino silver iodobromide emulsion. One of said photosensitive elements was coated at a coverage of 20 mgs/ft$^2$ of silver, and the other of said elements was coated at a coverage of 40 mgs/ft$^2$ of silver.

A second element containing a compound of the present invention was prepared employing a component similar to that described in U.S. Pat. No. 3,647,437 (column 66, lines 46 to 59) which comprised a transparent polyethylene terephthalate film base carrying the following layers.

(1) a polymeric acid layer
(2) a polymeric spacer (timing) layer
(3) a polymeric image-receiving layer.

To form said second element, the above component was coated (over the image-receiving layer) with (a) 100 mgs/ft$^2$ of poly-4-vinylpyridine containing 100 mgs/ft$^2$ of the colorless image dye-providing compound of Example 1 (or 100 mgs/ft$^2$ of the colorless image dye-providing compound of Example 2) and (b) 30 mgs/ft$^2$ of gelatin containing succindialdehyde hardener.

The photosensitive elements were given an exposure through a stepwedge to white light of 2 mcs and superposed with said second elements. A layer of an aqueous alkaline processing composition approximately 0.0020 inch thick was distributed between said elements by passing the film units between a pair of pressure-applying rolls in the dark. The processing composition comprised the following ingredients.

Water 100 cc
Potassium hydroxide 5 g
Sodium sulfite 2 g
6-methylthiomethyl-2,4-dihydroxy-purimidine 1.5 g
Tetramethyl reductic acid 6 g
Hydroxyethyl cellulose 3 g
Titanium dioxide 50 g After applying said processing composition the film units were maintained intact to provide an integral negative-positive reflection print, and at recorded time intervals, the maximum and minimum reflection densities were measured for the positive yellow images. The densities measured at given times are set forth in Table I below.

TABLE I

| Cpd of Ex. 1 (20 mgs/ft$^2$ Ag) | | Cpd of Ex. 1 (40 mgs/ft$^2$ Ag) | | Cpd of Ex. 2 (40 mgs/ft$^2$ Ag) | |
|---|---|---|---|---|---|
| Time | Dmax/Dmin | Time | Dmax/Dmin | Time | Dmax/Dmin |
| 10 min | 0.37/0.25 | 10 min | — | 10 min | 0.38/0.33 |
| 20 min | 0.40/0.27 | 20 min | 0.44/0.24 | — | — |
| 30 min | 0.40/0.27 | — | — | — | — |
| 40 min | 0.41/0.27 | 75 min | 0.49/0.27 | 40 min | 0.50/0.32 |
| 2.5 hrs | 0.47/0.28 | 3.5 hrs | 0.52/0.29 | 2.5 hrs | 0.95/0.52 |
| 18 hrs | hrs | 18 min | 0.64/0.56 | — | — |

EXAMPLE II

A photosensitive element was prepared by coating a gelatin subcoated polyethylene terephthalate film base with a gelatino silver iodobromide emulsion at a coverage of 40 mgs/ft² of silver.

A second element was prepared in the same manner described in Example I above except that the coating (a) contained 150 mgs/ft² of the compound of Example 4 in 100 mgs/ft² of poly-4-vinylpyridine.

The unexposed photosensitive element was superposed with said second element and one-half of the resulting sandwich was processed with a layer (0.0020 inch thick) of an aqueous 5% sodium hydroxide solution containing 3% of hydroxyethyl cellulose and the other half of the sandwich was processed with a layer (0.0020 inch thick) of an aqueous 5% sodium hydroxide solution containing 1.5% of 6-methylthiomethyl-2,4-dihydroxypyrimidine silver halide solvent and 3% of hydroxyethyl cellulose. The optical transmission densities were measured at given time intervals for the two halves of the sandwich and showed the formation of dye from the colorless precursor. The results obtained are set forth in Table II below.

TABLE II

| Time | Optical Transmission Density | |
| (min.) | Without Solvent | With Solvent |
| --- | --- | --- |
| 10 | 0.27 | 0.27 |
| 27 | 0.24 | 0.32 |
| 39 | 0.25 | 0.55 |
| 57 | 0.28 | 0.73 |

EXAMPLE III

A photosensitive element was prepared by coating a transparent polyethylene terephthalate film base with the following layers.

(1) a layer containing 50 mgs/ft² of poly-4-vinylpyridine and 150 mgs/ft² of the compound of Example 3, (2) a layer of gelatin coated at a coverage of 100 mgs/ft², (3) a gelatino silver iodobromide emulsion layer coated at a coverage of 60 mgs/ft² of silver, and (4) a layer of gelatin containing succindialdehyde.

To show the formation of dye in the presence of silver halide complex, the unexposed photosensitive element was superposed with a second element similar to that described in U.S. Pat. No. 3,647,437 (column 66, lines 46 to 59) which comprised a transparent polyethylene terephthalate film base carrying the following layers.

(1) a polymeric acid layer
(2) a polymeric spacer (timing) layer
(3) a polymeric image-receiving layer.

The superposed elements were processed in the same manner using the same two processing compositions as in Example II above to show the formation of dye from the colorless precursor in the presence of silver halide complex. The optical transmission densities that were measured at given time intervals are set forth in Table III below.

TABLE III

| Time | Optical Transmission Density | |
| | Without Solvent | With Solvent |
| --- | --- | --- |
| 1 min. | 0.13 | 0.14 |
| 3 min. | 0.14 | 0.15 |
| 10 min. | 0.18 | 0.20 |
| 1 hr | 0.17 | 0.26 |
| 1 day | 0.26 | 0.36 |
| 7 day | 0.45 | 0.60 |

It will be appreciated that the photographic systems of the present invention for providing an imagewise distribution of a photographic reagent may be used to provide dyes, dye intermediates and photographic reagents other than those specifically mentioned. Also, it will be appreciated that the present systems may be used with film structures other than those illustrated.

Since certain changes may be made in the herein-defined subject matter without departing from the scope of the invention herein involved, it is intended that all matter contained in the above description should be interpreted as illustrative and not in a limiting sense.

What is claimed is:

1. A photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ions and/or soluble silver complex in the partially developed and undeveloped areas of said emulsion; and forming as a function of said development a color image in dye from said colorless precursor, said colorless precursor of a preformed image dye being substituted with a moiety containing a thiazolidinyl group, said thiazolidinyl group (a) being capable of undergoing cleavage in the presence of said silver ions and/or soluble silver complex and (b) possessing a substituent on the carbon atom in the 2-position that undergoes a $\beta$-elimination reaction following the cleavage of said thiazolidinyl group, said moiety maintaining said precursor in its colorless form at least until said thiazolidinyl group undergoes said cleavage.

2. A process as defined in claim 1 wherein said image dye is substantially non-diffusible from the layer in which it is positioned during said photoexposure.

3. A process as defined in claim 1 wherein said colorless precursor is substantially non-diffusible from the layer in which it is positioned during said photoexposure.

4. A process as defined in claim 3 wherein said colorless precursor is positioned in said silver halide emulsion during photoexposure.

5. A process as defined in claim 1 wherein said image dye provided by said colorless precursor is diffusible, said process including the step of transferring said diffusible image dye to an image-receiving layer in superposed relationship with said silver halide emulsion.

6. A process as defined in claim 5 wherein a light-reflecting layer is provided between said silver halide emulsion and said image-receiving layer, whereby said dye image may be viewed against said light-reflecting layer, said light-reflecting layer being effective to mask said developed silver halide emulsion from one viewing said dye image.

7. A process as defined in claim 1 wherein said silver halide emulsion is a negative working silver halide emulsion whereby a positive color image is formed as a function of said development.

8. A photographic product comprising a photosensitive element comprising a plurality of layers including a support; a silver halide emulsion in a layer on said support; and in a layer on the same side of said support as said silver halide emulsion, a colorless precursor of a preformed image dye substituted with a moiety containing a thiazolidinyl group, said thiazolidinyl group (a)

being capable of undergoing cleavage in the presence of silver ions and/or soluble silver complex and (b) possessing a substituent on the carbon atom in the 2-position that undergoes a β-elimination reaction following the cleavage of said thiazolidinyl group, said moiety maintaining said precursor in its colorless form at least until said thiazolidinyl group undergoes said cleavage.

9. A photographic product as defined in claim 8 wherein said colorless precursor is non-diffusible in aqueous alkaline solution.

10. A photographic product as defined in claim 8 wherein said image dye provided by said colorless precursor is non-diffusible in aqueous alkaline solution.

11. A photographic product as defined in claim 8 wherein said image dye provided by said colorless precursor is diffusible in aqueous alkaline solution and said product includes an image-receiving layer so positioned as to be capable of receiving by diffusion said imagewise distribution of said diffusible dye.

12. A photographic product as defined in claim 11 which additionally includes means for applying an aqueous processing composition to provide an aqueous alkaline solution of a silver halide developing and a silver halide solvent.

13. A photographic product as defined in claim 11 which includes a light-reflecting layer between said silver halide emulsion and said image-receiving layer, whereby said dye image formed by said imagewise distribution of diffusible dye may be viewed by reflection, said light-reflecting layer being effective to mask said developed silver halide emulsion from one viewing said dye image.

14. A photographic product as defined in claim 8 wherein said colorless precursor is positioned in said silver halide emulsion.

15. A photographic product as defined in claim 8 which includes a silver halide developing agent in said silver halide emulsion layer.

16. A photographic product as defined in claim 15 which includes a silver halide solvent in a layer on the same side of the support as said silver halide emulsion.

17. A photographic product as defined in claim 8 wherein said silver halide emulsion is a negative working emulsion.

18. A photographic product as defined in claim 8 which additionally includes an acid-reacting layer.

19. A photographic process for providing an imagewise distribution of a photographically useful reagent, which process includes the steps of developing a photosensitive element comprising an exposed silver halide emulsion with an aqueous alkaline processing composition; forming in partially developed and in undeveloped areas an imagewise distribution of silver ions and/or soluble silver complex; contacting said imagewise ditribution of silver ions and/or soluble silver complex with a compound comprising the radical of a photographically useful reagent substituted with a moiety containing a thiazolidinyl group, said thiazolidinyl group (a) being capable of undergoing cleavage in that presence of said silver ions and/or soluble silver complex and (b) possessing a substituent on the carbon atom in the 2-position that undergoes a β-elimination reaction following by the cleavage of said thiazolidinyl group to provide said photographically useful reagent as a carbamic acid; and forming as a function of contacting said imagewise distribution of said silver ions and/or soluble silver complex with said compound, a corresponding imagewise distribution of said photographically useful reagent.

20. A process as defined in claim 19 wherein said radical of a photographically useful reagent is selected from a photographically active reagent and a color-providing moiety.

21. A process as defined in claim 20 wherein said radical of a photographically useful reagent is a photographically active reagent.

22. A process as defined in claim 20 wherein said radical of a photographically useful reagent is a color-providing moiety.

23. A process as defined in claim 22 wherein said color-providing moiety is the colorless precursor of a preformed image dye and said moiety containing the thiazolidinyl group maintains said precursor in its colorless form at least until said thiazolidinyl group undergoes said cleavage to activate said β-elimination reaction to provide a dye image.

24. A photographic product comprising a photosensitive element comprising a plurality of layers including a support; a silver halide emulsion in a layer on said support; and in a layer on the same side of said support as said silver halide emulsion, a compound comprising the radical of a photographically useful reagent substituted with a moiety containing a thiazolidinyl group, said thiazolidinyl group (a) being capable of undergoing cleavage in the presence of silver ions and/or soluble silver complex and (b) possessing a substituent on the carbon atom in the 2-position that undergoes a β-elimination reaction followed by the cleavage of said thiazolidinyl group to provide said photographically useful reagent as a carbamic acid.

25. A photographic product comprising first and second sheetlike elements, said first element comprising a plurality of layers including a support; a photosensitive silver halide emulsion in a layer on said support; in a layer in one of said first and second sheetlike elements, a compound comprising the radical of a photographically useful reagent substituted with a moiety containing a thiazolidinyl group, said thiazolidinyl group (a) being capable of undergoing cleavage in the presence of silver ions and/or soluble silver complex and (b) possessing a substituent on the carbon atom in the 2-position that undergoes a β-elimination reaction activated by the cleavage of said thiazolidinyl group to provide said photographically useful reagent as a carbamic acid; and means for applying an aqueous alkaline processing composition to provide a silver halide developing agent and a silver halide solvent in a substantially uniform layer between said emulsion layer and said second sheetlike element in superposed relationship therewith.

\* \* \* \* \*